United States Patent [19]

Garren

[11] Patent Number: 4,953,566
[45] Date of Patent: Sep. 4, 1990

[54] BODY WRAP FOR USE IN DIAGNOSTIC PROCEDURE

[76] Inventor: Lloyd R. Garren, P.O. Box 3738, Wilmington, Del. 19807

[21] Appl. No.: 337,939

[22] Filed: May 18, 1989

[51] Int. Cl.$^5$ ............................................. A61F 13/00
[52] U.S. Cl. ................................................... 128/849
[58] Field of Search ............................... 128/849–854; 2/DIG. 6, DIG. 7; 604/394, 395

[56] References Cited

U.S. PATENT DOCUMENTS

| | | |
|---|---|---|
| 1,724,443 | 8/1929 | Wheeler . |
| 3,364,928 | 1/1968 | Creager, Jr. et al. . |
| 3,422,817 | 1/1969 | Mishkin et al. . |
| 3,452,750 | 7/1969 | Blanford . |
| 3,800,790 | 4/1974 | Collins ............................ 128/854 |
| 3,860,003 | 1/1975 | Buell . |
| 4,336,797 | 6/1982 | Latucca et al. .................. 128/854 |
| 4,446,575 | 5/1984 | Davis ................................... 2/400 |
| 4,515,595 | 5/1985 | Kievit . |
| 4,520,807 | 6/1985 | Rotter . |
| 4,570,628 | 2/1986 | Neal . |
| 4,573,986 | 3/1986 | Minetola . |
| 4,578,071 | 3/1986 | Buell . |
| 4,596,245 | 6/1986 | Morris . |
| 4,820,296 | 4/1989 | Masliyah ........................... 604/394 |
| 4,834,737 | 5/1989 | Khan ............................. 604/385.2 |

Primary Examiner—Robert A. Hafer
Assistant Examiner—Kerry Owens
Attorney, Agent, or Firm—Connolly & Hutz

[57] ABSTRACT

A disposable body wrap is configured to be worn by a person in the manner of a diaper while the person is undergoing rectal examination. The wrap comprises a sheet having front and back area portions interconnected to a crotch area portion. Each of the front and back area portions has a waistband, and structure is provided for releasably securing these waistband portions together around the waist of the person wearing the wrap. A small access opening in the crotch area portion of the sheet is positioned and dimensioned to permit instrumentation to pass therethrough for rectal examination. A flap on the outside of the sheet covers the small access opening in the crotch area portion, and this flap also has a small access opening therein positioned and dimensioned to permit instrumentation to pass therethrough for examination purposes. The wrap reduces professional risk involved in performing the examination.

3 Claims, 2 Drawing Sheets

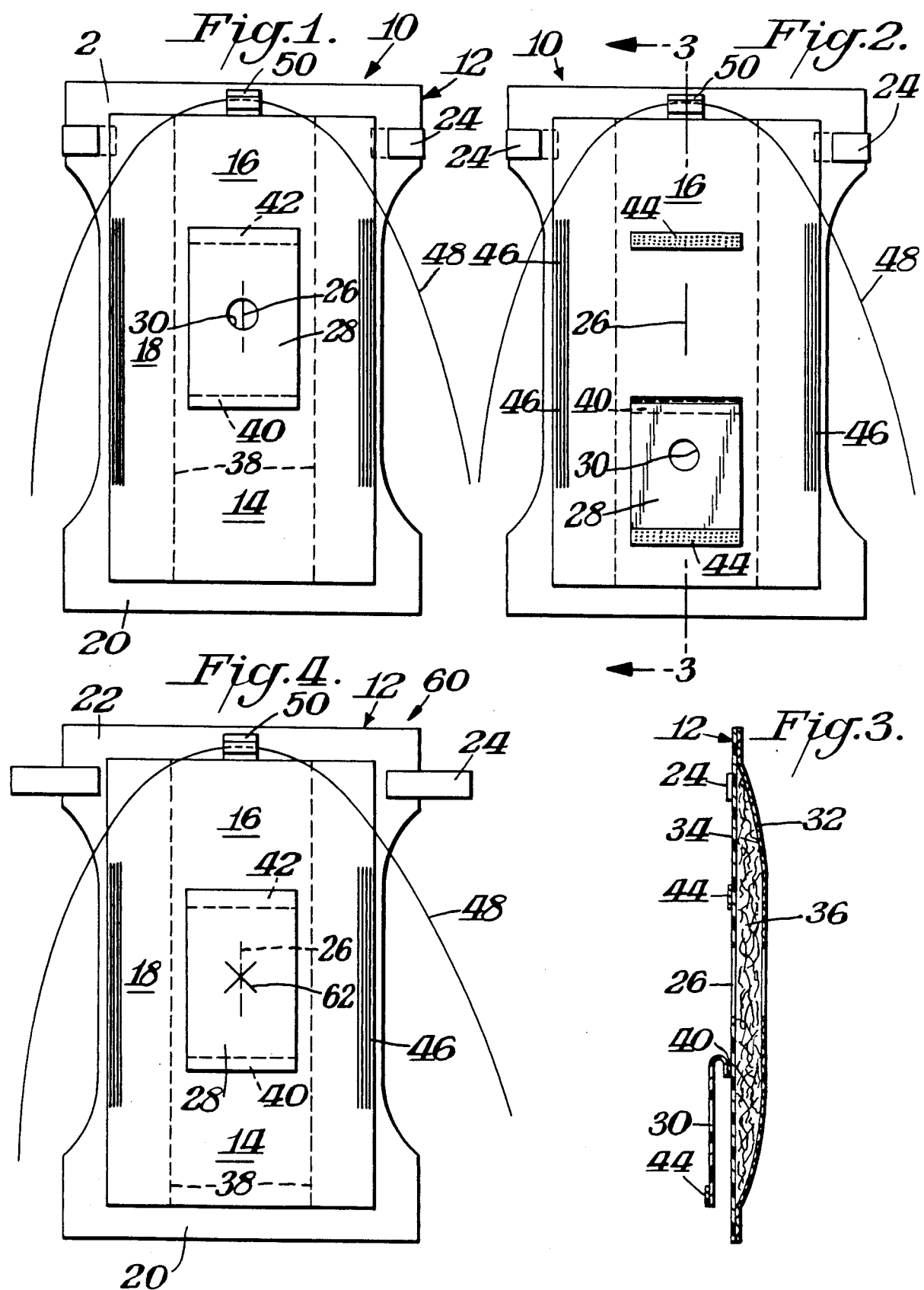

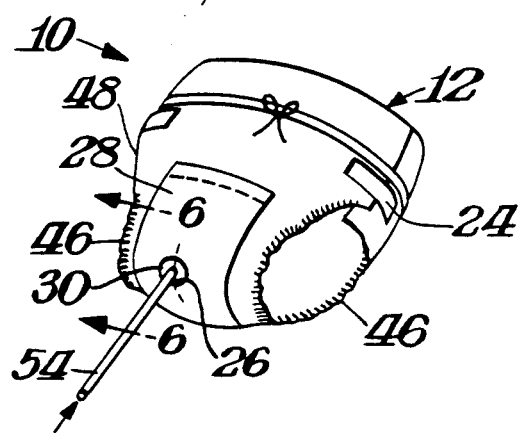
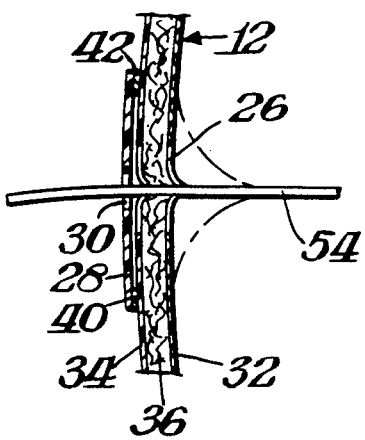
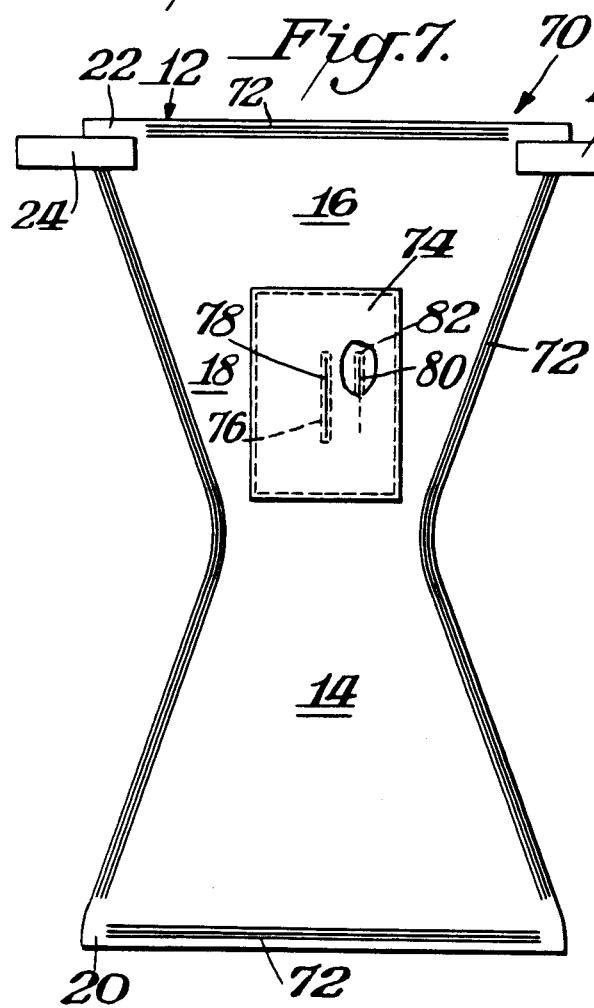
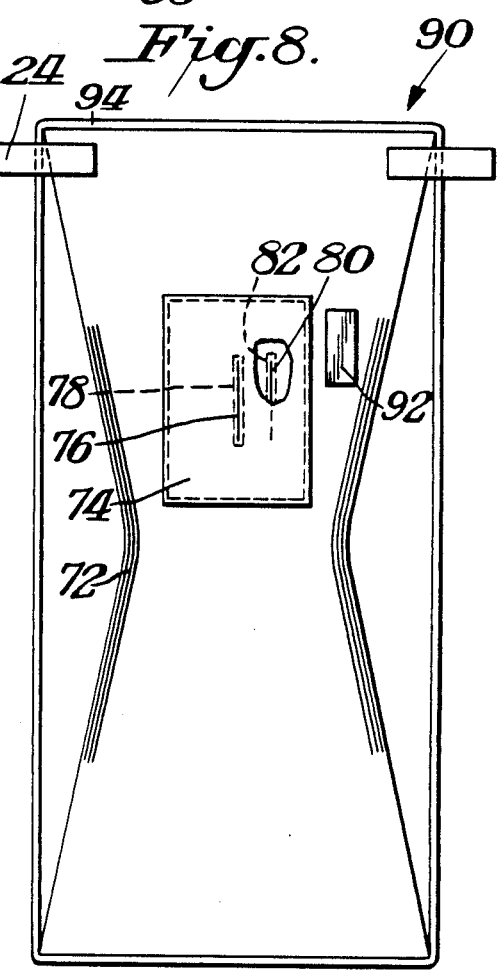

BODY WRAP FOR USE IN DIAGNOSTIC PROCEDURE

BACKGROUND OF THE INVENTION

The present invention relates to a disposable body wrap for use by a person undergoing rectal examination which permits instrumentation to pass therethrough while protecting the person conducting the diagnostic procedure from possible contamination.

Colonoscopy, sigmoidoscopy, and barium enema are procedures which all have in common the introduction of a tube into the rectum and the insertion of a fluid medium (air or liquid) into the bowel. These procedures are done for either diagnostic or therapeutic reasons. Since there is an instrument in the anal canal and a fluid medium is introduced, there is developed a back pressure which often causes fluid (from both exogenous and endogenous sources) contamination of the local region and the professional performing the procedures. There are numerous diseases which can be transmitted via this type of contamination with feces and body fluids emanating from the colon. No effective barriers have been developed to date.

SUMMARY OF THE INVENTION

Accordingly, it is an object of the present invention to provide a body wrap for use by persons undergoing rectal examination which limits and contains the area of contamination and helps reduce professional risk involved in performing these procedures.

In accordance with the present invention, a disposable body wrap is configured to be worn by a person in the manner of a diaper during diagnostic and therapeutic procedures requiring instrumentation of the rectum. The body wrap protects the professional from contamination during these procedures. Specifically, the body wrap of the present invention comprises a sheet having front and back area portions interconnected by a crotch area portion. Each of the front and back area portions has a waistband portion, and structure is provided for releasably securing these waistband portions together around the waist of a person wearing the body wrap. A small access opening in the crotch area portion of the sheet is positioned and dimensioned to permit instrumentation to pass therethrough for rectal examination of the person undergoing the procedure. A flap on the outside of the sheet functions to cover the small access opening in the crotch area portion. The flap also has a small access opening therein positioned and dimensioned to permit instrumentation to pass therethrough for rectal examination purposes.

The structure for releasably securing the waistband portions together may comprise tabs with adhesive thereon. Also, the sheet may comprise inner and outer layers with absorbent material disposed therebetween.

The small access opening in the crotch area of the sheet may be in the form of a slit and the opening in the flap may be generally circular and in alignment with that slit. Alternatively, the access opening in the flap may be x-shaped and in alignment with the slit. In another embodiment each of the access openings comprises a slit. These slits may be parallel to one another and slightly offset.

In one or more embodiments of the present invention the flap may have a first pair of opposite edges secured to the outside of the sheet. One edge may be fixedly secured to the sheet with the other edge releasably secured thereto. Alternatively, the entire periphery of the flap may be secured to the outside of the sheet.

Preferably, the crotch area portion of the sheet has elastic secured thereto along opposite side edges. Moreover, the overall sheet construction may have elastic secured thereto along the entire periphery of the sheet. Also, separate elastic strings may extend between the ends of the waistband portions to thereby provide leg holes to facilitate positioning the body wrap around the person.

BRIEF DESCRIPTION OF THE DRAWING

Novel features and advantages of the present invention in addition to those noted above will become apparent to those of ordinary skill in the art from a reading of the following detailed description in conjunction with the accompanying drawing wherein similar reference characters refer to similar parts and in which:

FIG. 1 is a top plan view of a body wrap used for diagnostic or therapeutic procedures which require instrumentation of the rectum, according to the present invention;

FIG. 2 is a top plan view similar to FIG. 1 but illustrating the cover flap in its open position;

FIG. 3 is a cross-sectional view taken along 3—3 of FIG. 2;

FIG. 4 is a top plan view illustrating another embodiment of a body wrap wherein the flap thereof is permanently secured along opposite edges;

FIG. 5 is a perspective view illustrating the body wrap of FIGS. 1-3 in its operative position;

FIG. 6 is a fragmental cross-sectional view taken along line 6—6 of FIG. 5;

FIG. 7 is a top plan view of still another body wrap, according to the present invention; and FIG. 8 is a top plan view of still another body wrap, according to the present invention, this one having elastic strings interconnecting the front and back area portions thereof at the sides.

DETAILED DESCRIPTION OF THE INVENTION

Referring in more particularity to the drawing, FIGS. 1-3 and 5-6 illustrate the first embodiment of the invention and specifically show a disposable body wrap 10 for use by a person undergoing diagnostic or therapeutic procedures which require instrumentation of the rectum. Body wrap 10 is worn by the person undergoing these procedures in a manner similar to that of a diaper. The physician or other professional normally conducting the procedure is thereby protected from any contamination which may result from the procedure.

Disposable body wrap 10 comprises a sheet of flexible material such as coated polypropylene for example, and the sheet is basically divided into a front area portion 14, a back area portion 16 and an interconnecting crotch area portion 18. Each of the front and back area portions has a waistband portion 20, 22 and these waistband portions may be releasably secured to one another around the waist of the person wearing the body wrap and undergoing examination. In the embodiment of FIGS. 1-3, tabs 24 of adhesive material are utilized for this purpose, as is well known in the diaper art.

The crotch area portion 18 includes a small access opening 26 in the form of a slit positioned and dimensioned to permit instrumentation to pass therethrough for rectal examination of the person wearing the body wrap. A flap 28 on the outside of the sheet 12 covers the small access opening 24 in the crotch area portion. The flap also has a small access opening 30 which is positioned and dimensioned to permit instrumentation to pass therethrough for rectal examination purposes, as explained more fully below.

As shown best in FIG. 3, sheet 12 generally comprises an inner layer 32 and an outer layer 34 heat sealed together along the outer boundary of the sheet. Absorbent material 36 is positioned between the inner and outer layers 32, 34 in the central area of the wrap as defined in part by the dashed lines 38 in FIGS. 1 and 2.

Flap 28 has a pair of opposite edge portions secured to the outside of sheet 12. Edge portion 40 is fixedly secured to the sheet while opposite edge portion 42 is releasably secured to the sheet by means of a velcro type fastening construction 44, for example. This arrangement of the flap facilitates use of the body wrap and insertion of instrumentation through both the circular opening 30 in the flap and the slit 26 in the sheet 12.

The crotch area portion 18 of sheet 12 has elastic material 46 secured thereto along the opposite side edges of that area portion. Elastic material 46 functions to gather the sheet and hold it securely against the legs of the person undergoing examination. Additionally, body wrap 10 includes a flexible string 48 secured at location 50 to the waistband portion 22 of the back area portion 16 of sheet 12. In use, after the wrap is positioned around the wearer and the tabs 24 used to secure the front and back area portions together, the flexible string is manipulated two turns around the waist of the person and the ends thereof tied together, as best shown in FIG. 5. Instrumentation 54 is then manipulated, as shown.

FIG. 4 illustrates another embodiment 60 of the present invention which is similar in many respects of the body wrap 10 of FIGS. 1-3. Accordingly, similar reference characters are utilized to identify similar parts Wrap 60 is different in that the flap 28 includes an x-shaped access opening 62 therein. Instrumentation passes through the x-shaped opening 62 and then through the opening 26 of sheet 12. Also, edge portion 42 is permanently secured to the sheet 12 in the same manner as edge portion 40 and no velcro is used.

FIG. 7 illustrates another body wrap 70 according to the present invention which is similar in some respects to the previously described raps 10, 60. However, in body wrap 70 sheet 12 simply comprises a single layer of coated polypropylene and elastic material 72 is disposed around the entire periphery thereof including the waistband portions 20,22. Additionally, body wrap 70 includes a flap 74 secured to the crotch area portion 18 of sheet 12 along the entire periphery of the flap. The small access opening in flap 74 is in the form of a slit 76 having elastic 78 sewn into the flap around and adjacent to the slit. The access opening in sheet 12 is also in the form of a slit 80 having elastic 82 sewn into the sheet around and adjacent to the slit.

As shown in FIG. 7, the slit shaped openings 76 and 80 are parallel to one another and slightly offset relative to one another. The instrumentation used for rectal examination first passes through opening 76 and then through opening 80 to thereby provide an effective barrier during the examination procedure. The elastic material 78, 82 disposed around these openings gathers the flap and sheet material around the instrumentation to provide an effective seal.

FIG. 8 illustrates another body wrap 90 which is very similar to body wrap 70 particularly in the construction of the flap thereof and the small access openings in both the flap and the crotch area of the sheet. A tab 92 having adhesive thereon is positioned next to the flap in order to assist in releasably securing tubing (not shown) which may be used during the diagnostic or therapeutic procedure.

Additionally, body wrap 90 includes 94 elastic material at the front and back waistband portions of sheet 12 secured along the edge of these waistband portions. The elastic material 94 in string form interconnects the ends of the front and back waistband portions along the right and left sides thereof, as shown in FIG. 8. These elastic strings provide leg holes into which the legs of the wearer are initially inserted in order to facilitate securing body wrap 90 in place. After such positioning of the legs, the front and back area portions are appropriately positioned and the tabs 24 are used to secure the front and back waistband portions together. Instrumentation may then be passed through the access openings 76, 80 to conduct the examination while the body wrap 90 functions to protect the physician or other professional performing the diagnostic or therapeutic procedure from contamination.

What is claimed is:

1. A disposable body wrap configured to be worn by a person in the manner of a diaper, the body wrap comprising a sheet having front and back area portions interconnected by a crotch area portion, each of the front and back area portions having a waistband portion and means for releasably securing these waistband portions together around the waist of a person wearing the body wrap, a small access opening in the form of a slit in the crotch area portion of the sheet positioned and dimensioned to permit instrumentation to pass therethrough for rectal examination of a person wearing the body wrap, and a flap on the outside of the sheet covering the small access opening in the crotch area portion, the flap having first and second pairs of opposite edges fixedly secured to the outside of the sheet and also having a small access opening in the form of a slit offset and parallel to the slit in the sheet positioned and dimensioned to permit instrumentation to pass therethrough for rectal examination purposes.

2. A disposable body wrap configured to be worn by a person in the manner of a diaper, the body wrap comprising a sheet having front and back area portions interconnected by a crotch area portion, each of the front and back area portions having a waistband portion and means for releasably securing these waistband portions together around the waist of a person wearing the body wrap, a small access opening in the form of a slit in the crotch area portion of the sheet positioned and dimensioned to permit instrumentation to pass therethrough for rectal examination of a person wearing the body wrap, and a flap on the outside of the sheet covering the small access opening in the crotch area portion, the flap also having a small access opening in the form of a slit offset fan parallel to the slit in the sheet positioned and dimensioned to permit instrumentation to pass therethrough for rectal examination purposes.

3. A disposable body wrap configured to be worn by a person in the manner of a diaper, the body wrap comprising a sheet having front and back area portions interconnected by a crotch area portion, each of the front and back area portions having a waistband portion and means for releasably securing these waistband portions together around the waist of a person wearing the body wrap, a small access opening in the crotch area portion of the sheet positioned and dimensioned to permit instrumentation to pass therethrough for rectal examination of a person wearing the body wrap, and a flap on the outside of the sheet covering the small access opening in the crotch area portion, the flap also having a small access opening adjacent and offset relative to the opening in the sheet therein positioned and dimensioned to permit instrumentation to pass therethrough for rectal examination purposes.

* * * * *